US008849411B2

(12) United States Patent
Moffitt et al.

(10) Patent No.: US 8,849,411 B2
(45) Date of Patent: Sep. 30, 2014

(54) USER-DEFINED GRAPHICAL SHAPES USED AS A VISUALIZATION AID FOR STIMULATOR PROGRAMMING

(75) Inventors: Michael A. Moffitt, Valencia, CA (US); Dennis Zottola, Ventura, CA (US); Jim Cassidy, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 58 days.

(21) Appl. No.: 13/473,457

(22) Filed: May 16, 2012

(65) Prior Publication Data

US 2012/0296396 A1 Nov. 22, 2012

Related U.S. Application Data

(60) Provisional application No. 61/487,015, filed on May 17, 2011.

(51) Int. Cl.
*A61N 1/36* (2006.01)
*A61N 1/372* (2006.01)
*G06F 19/00* (2011.01)
*A61N 1/05* (2006.01)

(52) U.S. Cl.
CPC ........ *A61N 1/36128* (2013.01); *A61N 1/37247* (2013.01); *G06F 19/3406* (2013.01); *G06F 19/3481* (2013.01); *A61N 1/36185* (2013.01); *A61N 1/36067* (2013.01); *A61N 1/36064* (2013.01); *A61N 1/0534* (2013.01); *A61N 1/0531* (2013.01)
USPC .......................................................... 607/59

(58) Field of Classification Search
USPC .................................................. 607/46, 59
See application file for complete search history.

(56) References Cited

U.S. PATENT DOCUMENTS

| 6,516,227 | B1 | 2/2003 | Meadows et al. |
| 6,845,267 | B2 | 1/2005 | Harrison et al. |
| 6,895,280 | B2 | 5/2005 | Meadows et al. |

(Continued)

FOREIGN PATENT DOCUMENTS

WO    WO 2007/097860 A1    8/2007

OTHER PUBLICATIONS

Frankemolle, Anneke M.M. et al., Reversing cognitive-motor impairments in parkinson's disease patients using a computational modelling approach to deep brain stimulation programming, Brain 2010: 133; 746-761.

(Continued)

*Primary Examiner* — Carl H Layno
*Assistant Examiner* — Jon Eric C Morales
(74) *Attorney, Agent, or Firm* — Vista IP Law Group LLP

(57) ABSTRACT

A system for programming a neurostimulation device coupled to one or more electrodes. The system comprises a user interface configured for allowing a user to select a set of stimulation parameters and to define a graphical shape representative of an anatomical region of interest. The system further comprises memory configured for storing the graphical shape in registration with an anatomical reference, and output circuitry configured for communicating with the neurostimulation device. The system further comprises a controller configured for recalling the registered graphical shape and anatomical reference from the memory, generating display signals capable of prompting the user interface to concurrently display a representation of the electrode(s) relative to the recalled graphical shape and anatomical reference, and programming the neurostimulation device with the selected stimulation parameter set via the output circuitry.

22 Claims, 12 Drawing Sheets

(56) References Cited

U.S. PATENT DOCUMENTS

| | | |
|---|---|---|
| 6,950,707 B2 | 9/2005 | Whitehurst |
| 6,993,384 B2 | 1/2006 | Bradley et al. |
| 7,346,382 B2 | 3/2008 | McIntyre et al. |
| 7,650,184 B2 | 1/2010 | Walter |
| 8,019,439 B2 | 9/2011 | Kuzma et al. |
| 2004/0034394 A1 | 2/2004 | Woods et al. |
| 2006/0017749 A1* | 1/2006 | McIntyre et al. ............. 345/664 |
| 2007/0168004 A1 | 7/2007 | Walter |
| 2007/0168007 A1 | 7/2007 | Kuzma et al. |
| 2009/0287467 A1 | 11/2009 | Sparks et al. |
| 2010/0010566 A1 | 1/2010 | Thacker et al. |
| 2010/0121409 A1 | 5/2010 | Kothandaraman et al. |

OTHER PUBLICATIONS

PCT International Search Report for PCT/US2012/038196, Applicant: Boston Scientific Neuromodulation Corporation, Form PCT/ISA/210 and 220, dated Jul. 25, 2012 (4pages).

PCT Written Opinion of the International Search Authority for PCT/US2012/038196, Applicant: Boston Scientific Neuromodulation Corporation, Form PCT/ISA/237, dated Jul. 25, 2012 (4pages).

PCT International Preliminary Report on Patentability (Chapter I of the Patent Cooperation Treaty) for PCT/US2012/038196, Applicant: Boston Scientific Neuromodulation Corporation, Form PCT/IB/326 and 373, dated Nov. 28, 2013 (6pages).

* cited by examiner

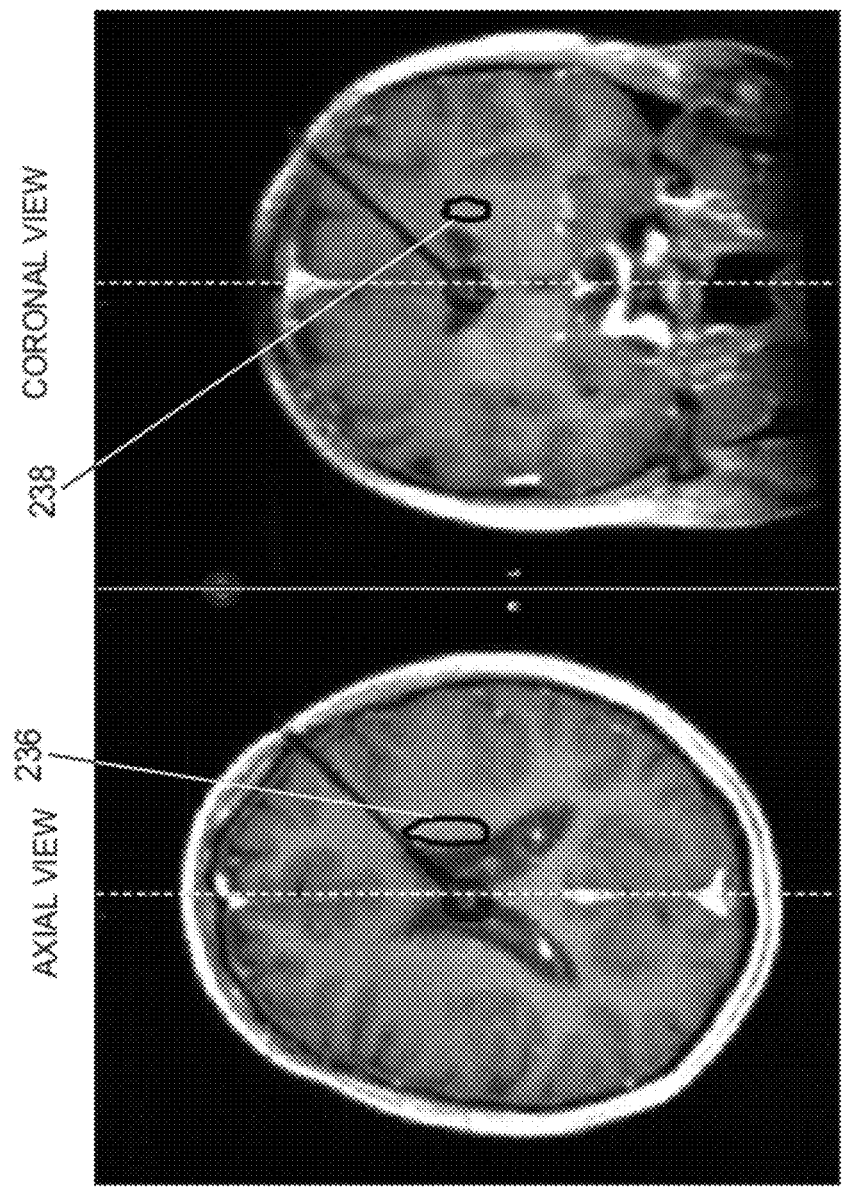

USER-DEFINED GRAPHICAL SHAPES USED AS A VISUALIZATION AID FOR STIMULATOR PROGRAMMING

RELATED APPLICATION DATA

The present application claims the benefit under 35 U.S.C. §119 to U.S. provisional patent application Ser. No. 61/487,015, filed May 17, 2011. The foregoing application is hereby incorporated by reference into the present application in its entirety.

FIELD OF THE INVENTION

The present invention relates to user-defined graphical shapes used as a visualization aid, and more particularly, to user-defined graphical shapes used as a visualization aid for stimulator programming.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications, such as angina pectoris and incontinence. Further, in recent investigations, Peripheral Nerve Stimulation (PNS) systems have demonstrated efficacy in the treatment of chronic pain syndromes and incontinence, and a number of additional applications are currently under investigation. More pertinent to the present inventions described herein, Deep Brain Stimulation (DBS) has been applied therapeutically for well over a decade for the treatment of neurological disorders, including Parkinson's Disease (PD), essential tremor, dystonia, and epilepsy, to name but a few. Further details discussing the treatment of diseases using DBS are disclosed in U.S. Pat. Nos. 6,845,267, 6,845,267, and 6,950,707, which are expressly incorporated herein by reference.

Each of these implantable neurostimulation systems typically includes one or more electrode carrying stimulation leads, which are implanted at the desired stimulation site, and a neurostimulator implanted remotely from the stimulation site, but coupled either directly to the neurostimulation lead(s) or indirectly to the neurostimulation lead(s) via a lead extension. A single stimulation lead may contain electrodes of different sizes. The neurostimulation system may further comprise a handheld external control device to remotely instruct the neurostimulator to generate electrical stimulation pulses in accordance with selected electrical stimulation parameters.

Electrical stimulation energy may be delivered from the neurostimulator to the electrodes in the form of an electrical pulsed waveform. Thus, the stimulation energy may be controllably delivered to the electrodes to stimulate the tissue. The combination of electrodes used to deliver the electrical pulses to the targeted tissue constitutes an electrode combination, with the electrodes capable of being selectively programmed to act as anodes (positive), cathodes (negative), and/or left off (zero). In other words, an electrode combination represents the polarity being positive, negative, or zero. Other parameters that may be controlled or varied include the amplitude, width, and rate of the electrical pulses provided through the electrode array. Each electrode combination, along with its electrical pulse parameters, can be referred to as a "stimulation parameter set."

With some neurostimulation systems, and in particular, those with independently controlled current and/or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e. fractionalized electrode combinations).

As briefly discussed above, an external control device can be used to instruct the neurostimulator to generate electrical stimulation pulses in accordance with selected stimulation parameters. Typically, the stimulation parameters programmed into the neurostimulator can be adjusted by the user by manipulating controls on the external user control device to modify the electrical stimulation provided by the neurostimulator system to the patient. Thus, in accordance with the stimulation parameters programmed by the external control device, electrical pulses can be delivered from the neurostimulator to the stimulation electrode(s) to stimulate or activate a volume of tissue in accordance with the set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of pain), while minimizing the amount of non-target tissue that is stimulated. A typical stimulation parameter set may include the electrodes that acting as anodes or cathodes, as well as the amplitude, duration, and rate of the stimulation pulses.

To facilitate the selection of the stimulation parameters, the clinician generally programs the external control device, and if applicable the neurostimulator, through a computerized programming system. This programming system can be a self-contained hardware/software system, or can be defined predominately by software that is run on a standard personal computer (PC). The PC or custom hardware may actively control the characteristics of the electrical stimulation generated by the neurostimulator to allow the optimum stimulation parameters to be determined based on patient feedback, or other means, and to subsequently program the external control device with the optimum electrical stimulation parameters.

When electrical leads are implanted within the patient, the computerized programming system may be used to instruct the neurotransmitter to apply electrical stimulation to test placement of the leads and/or electrodes, thereby assuring that the leads and/or electrodes are implanted in effective locations within the patient. Once the leads are correctly positioned, a fitting procedure, which may be referred to as a navigation session, may be performed using the computerized programming system to program the external control device, and if applicable the neurostimulator, with a set of stimulation parameters that best addresses the disorder or painful site.

Programming a neurostimulator (e.g., a DBS stimulator for treating movement disorders) can be a laborious and time intensive process that can take many programming sessions over several months to complete. Some movement disorder centers may abstain from referring patients for DBS because the centers are not able to manage the large number of patient programming sessions that are required. Currently, neurostimulator programming systems are being developed to allow users to visualize the physical anatomical structures and stimulation fields in order to aid in the neurostimulator programming process. (See, e.g., U.S. Pat. No. 7,346,382). However, in some cases, the anatomical structure(s) related to the specific stimulation treatment may not precisely and correctly represent the "stimulation target". For example, in DBS for severe cases of Parkinson's Disease (PD), some researchers argue that the entire subthalmic nucleus (STN) itself is not the stimulation target, but rather a sub-section of the STN is the correct stimulation target. Conversely, other researchers argue that the fields of forel are the correct stimulation target for treating severe PD, and yet other researchers argue that the zona inserta is the correct stimulation target.

Other prior art DBS stimulation techniques choose a stimulation target region based on an analysis of data from a population study. These DBS techniques also allow the target region to be visualized by the user programmer during the programming of the neurostimulator. However, as previously mentioned above, in some cases, not all researchers agree on a specific anatomical target region for a particular stimulation treatment. As such, it is highly unlikely that all researchers will agree on a particular target region for a specific stimulation treatment that is derived from data from a population study. Most likely, individual researchers will have their own theories about which anatomical regions should be used as the stimulation target for particular stimulation treatments.

There, thus, remains a need for a neurostimulation system that allows a user to define a stimulation target region in a more flexible manner.

SUMMARY OF THE INVENTION

In accordance with the present inventions, a system for programming a neurostimulation device coupled to one or more electrodes is provided.

The system comprises a user interface configured for allowing a user to select a set of stimulation parameters and to define a graphical shape representative of an anatomical region of interest (e.g., a therapy region or a side-effect region). The defined graphical shape may be, e.g., a three-dimensional graphical shape, such as an ellipsoid, a cuboid, or a pyramid.

The system further comprises memory configured for storing the graphical shape in registration with an anatomical reference (e.g., an atlas or one or more anatomical reference points, such as a posterior commissural point, anterior commissural point, and/or a mid-commissural point), and output circuitry (e.g., telemetry circuitry) configured for communicating with the neurostimulation device.

In one embodiment, the memory stores a plurality of predefined graphical shapes respectively representing anatomical regions of interest, in which case, the user interface may further be configured for allowing the user to select the graphical shape from the plurality of predefined graphical shapes. In another embodiment, the user interface is configured for allowing the user to define the graphical shape by allowing the user to draw a two-dimensional graphical shape. In this case, the system may further comprise a processor configured for extrapolating a three-dimensional graphical shape from the drawn two-dimensional shape.

In still another embodiment, the user interface is configured for allowing the user to define the graphical shape by allowing the user to import a graphical shape from another device. In yet another embodiment, the system further comprises a processor configured for generating a stimulation field model based on the selected stimulation parameter set, and the user interface is configured for allowing the user to define the graphical shape by allowing the user to select the stimulation field model as the graphical shape. In yet another embodiment, the user interface is configured for allowing the user to define the graphical shape by allowing the user to apply a Boolean function to a plurality of predefined graphical shapes to create the defined graphical shape. In yet another embodiment, the user interface is further configured for allowing the user to define a location and/or change a size of the defined graphical shape relative to the representation of the one or more electrodes.

The system further comprises a controller configured for recalling the registered graphical shape and anatomical reference from the memory, generating display signals capable of prompting the user interface to concurrently display a representation of the electrode(s) relative to the recalled graphical shape and anatomical reference, and programming the neurostimulation device with the selected stimulation parameter set via the output circuitry. The system may optionally comprise a processor configured for generating a stimulation field model based on the selected stimulation parameter set, in which case, the controller may be configured for generating display signals capable of prompting the user interface to concurrently display the generated stimulation field model relative to the recalled graphical shape and anatomical reference. In another embodiment, the system further comprises an external control device comprising the user interface, memory, output circuitry, and controller.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 13 is a plan view of yet another embodiment of an anatomical region of interest definition screen generated by the CP of FIG. 6 for defining a graphical shape representative of an anatomical region of interest for subsequent visualization in the programming screen illustrated in FIG. 7.

DETAILED DESCRIPTION OF THE EMBODIMENTS

The description that follows relates to a deep brain stimulation (DBS) system. However, it is to be understood that the while the invention lends itself well to applications in DBS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a spinal cord stimulator, peripheral nerve stimulator, microstimulator, or in any other neural stimulator configured to treat urinary incontinence, sleep apnea, shoulder subluxation, headache, etc.

Figure 1:
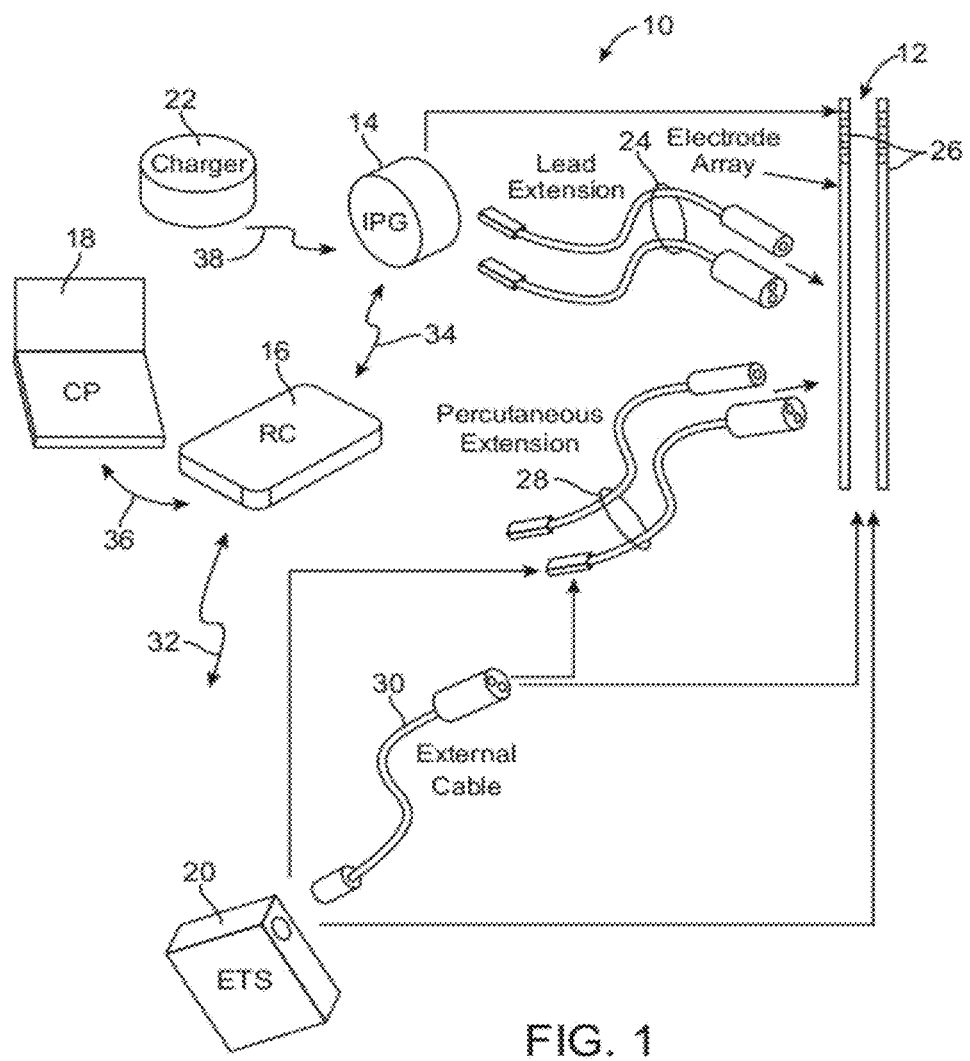
FIG. 1 is a plan view of a Deep Brain Stimulation (DBS) system constructed in accordance with one embodiment of the present inventions.

Turning first to FIG. 1, an exemplary DBS neurostimulation system 10 generally includes at least one implantable stimulation lead 12 (in this case, two), a neurostimulator in the form of an implantable pulse generator (IPG) 14, an external remote controller RC 16, a clinician's programmer (CP) 18, an External Trial Stimulator (electrodes ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 may be arranged in-line along the neurostimulation leads 12. In alternative embodiments, the electrodes 26 may be arranged in a two-dimensional pattern on a single paddle lead if, e.g., cortical brain stimulation is desired. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
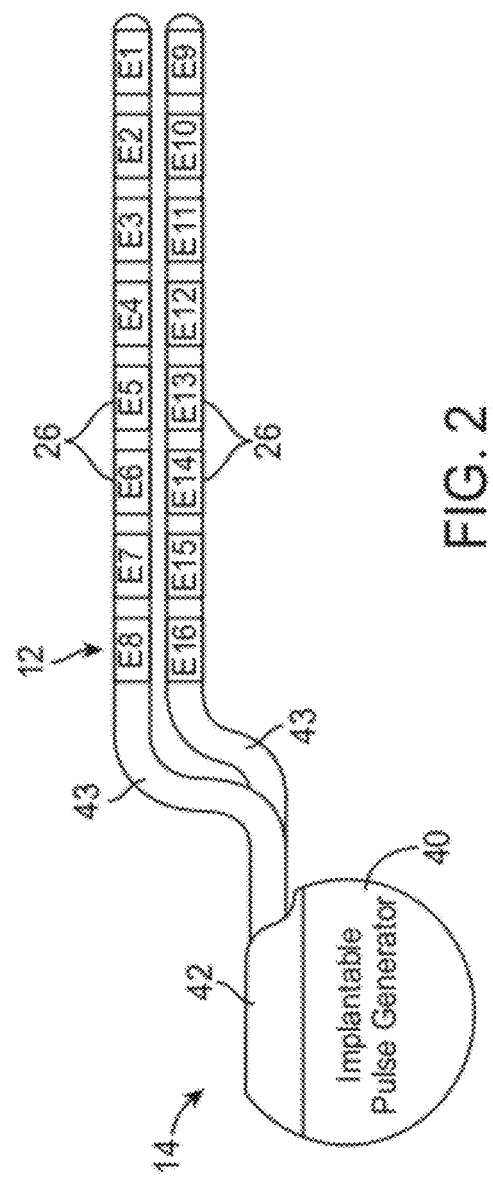
FIG. 2 is a perspective view of the arrangement of the DBS system of FIG. 1 with respect to a patient.

Referring to FIG. 2, the IPG 14 comprises an outer case 40 for housing the electronic and other components (described in further detail below), and a connector 42 to which the proximal end of the neurostimulation lead 12 mates in a manner that electrically couples the electrodes 26 to the internal electronics (described in further detail below) within the outer case 40. Although extensions 28 will typically be connected between the IPG 14 and the neurostimulation leads 12, the extensions 28 are not shown in FIG. 2 for purposes of brevity. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

Each of the neurostimulation leads 12 comprises an elongated cylindrical lead body 43, and the electrodes 26 take the form of ring electrodes mounted around the lead body 43. One of the neurostimulation leads 12 has eight electrodes 26 (labeled E1-E8), and the other neurostimulation lead 12 has eight electrodes 26 (labeled E9-E16). The actual number and shape of leads and electrodes will, of course, vary according to the intended application.

Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

As briefly discussed above, the IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse duration (measured in microseconds), pulse rate (measured in pulses per second), and burst rate (measured as the stimulation on duration X and stimulation off duration Y). The IPG 14 may be capable of delivering the stimulation energy to the array 22 over multiple channels or over only a single channel Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. Multipolar stimulation occurs when at least three of the lead electrodes 26 are activated, e.g., two as anodes and the remaining one as a cathode, or two as cathodes and the remaining one as an anode In the illustrated embodiment, IPG 14 can individually control the magnitude of electrical current flowing through each of the electrodes. In this case, it is preferred to have use current generators, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention.

Further details discussing the structure and function of IPGs are described more fully in U.S. Pat. Nos. 6,516,227 and 6,993,384, which are expressly incorporated herein by reference.

Figure 3:
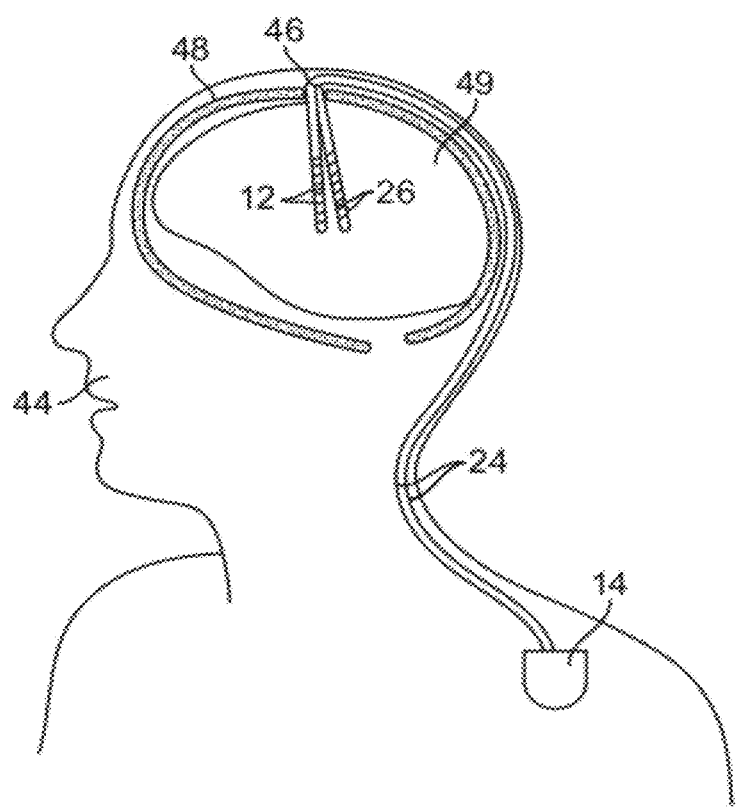
FIG. 3 is a profile view of an implantable pulse generator (IPG) and percutaneous leads used in the DBS system of FIG. 1.

As shown in FIG. 3, two percutaneous neurostimulation leads 12 are introduced through a burr hole 46 (or alternatively, two respective burr holes) formed in the cranium 48 of a patient 44, and introduced into the parenchyma of the brain 49 of the patient 44 in a conventional manner, such that the electrodes 26 are adjacent a target tissue region, the stimulation of which will treat the dysfunction (e.g., the ventrolateral thalamus, internal segment of globus pallidus, substantia nigra pars reticulata, subthalamic nucleus, or external segment of globus pallidus). Thus, stimulation energy can be conveyed from the electrodes 26 to the target tissue region to change the status of the dysfunction. Due to the lack of space near the location where the neurostimulation leads 12 exit the burr hole 46, the IPG 14 is generally implanted in a surgically-made pocket either in the chest, or in the abdomen. The IPG 14 may, of course, also be implanted in other locations of the patient's body. The lead extension(s) 24 facilitates locating the IPG 14 away from the exit point of the neurostimulation leads 12.

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the DBS system 10 may alternatively utilize an implantable receiver-stimulator (not shown) connected to the neurostimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 4:
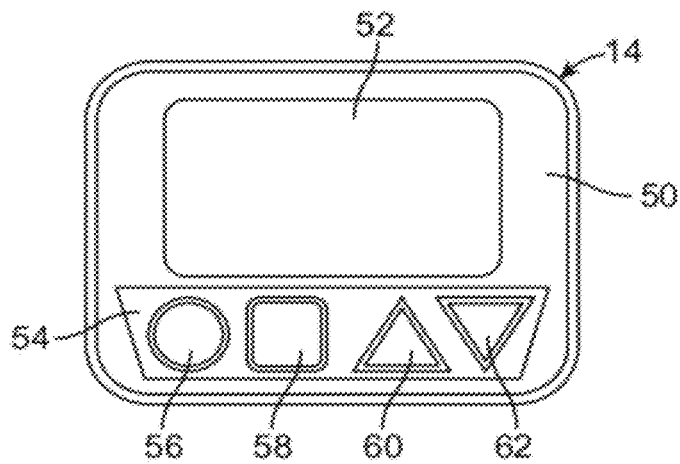
FIG. 4 is front view of a remote control (RC) used in the DBS system of FIG. 1.

Referring now to FIG. 4, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touch screen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can be actuated to increment or decrement any of stimulation parameters of the pulse generated by the IPG 14, including pulse amplitude, pulse width, and pulse rate. For example, the selection button 58 can be actuated to place the RC 16 in a "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 5:
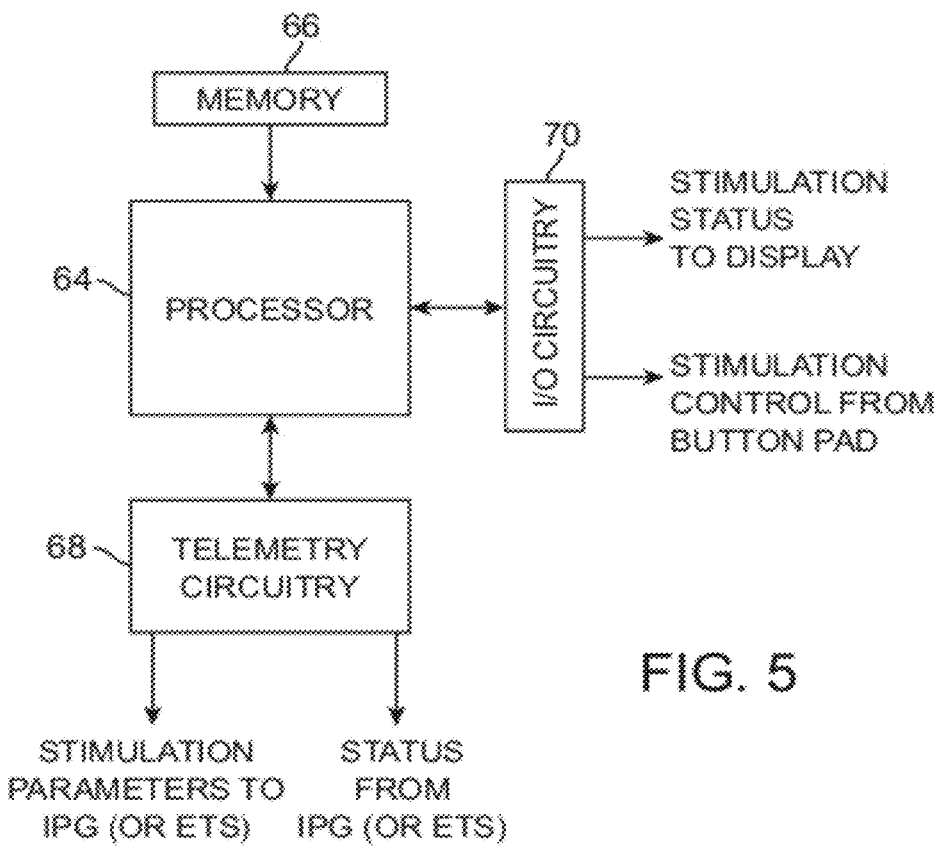
FIG. 5 is a block diagram of the internal components of the RC of FIG. 4.

Referring to FIG. 5, the internal components of an exemplary RC 16 will now be described. The RC 16 generally includes a controller/processor 64 (e.g., a microcontroller), memory 66 that stores an operating program for execution by the controller/processor 64, as well as stimulation parameter sets in a look-up table (described below), input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 4). As well as controlling other functions of the RC 16, which will not be described herein for purposes of brevity, the controller/processor 64 generates new stimulation parameter sets in response to the user operation of the button pad 54. These new stimulation parameter sets would then be transmitted to the IPG 14 (or ETS 20) via the telemetry circuitry 68. Further details of the functionality and internal componentry of the RC 16 are disclosed in U.S. Pat. No. 6,895,280, which has previously been incorporated herein by reference. Notably, while the controller/processor 64 is shown in FIG. 5 as a single device, the processing functions and controlling functions can be performed by a separate controller and processor.

As briefly discussed above, the CP 18 greatly simplifies the programming of multiple electrode combinations, allowing the physician or clinician to readily determine the desired stimulation parameters to be programmed into the IPG 14, as well as the RC 16. Thus, modification of the stimulation parameters in the programmable memory of the IPG 14 after implantation is performed by a clinician using the CP 18, which can directly communicate with the IPG 14 or indirectly communicate with the IPG 14 via the RC 16. That is, the CP 18 can be used by the physician or clinician to modify operating parameters of the electrode array 26 in the brain.

The overall appearance of the CP 18 is that of a laptop personal computer (PC), and in fact, may be implanted using a PC that has been appropriately configured to include a directional-programming device and programmed to perform the functions described herein. Alternatively, the CP 18 may take the form of a mini-computer, personal digital assistant (PDA), smartphone, etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient response and feedback and for subsequently programming the IPG 14 with the optimum stimulation parameters.

Figure 6:
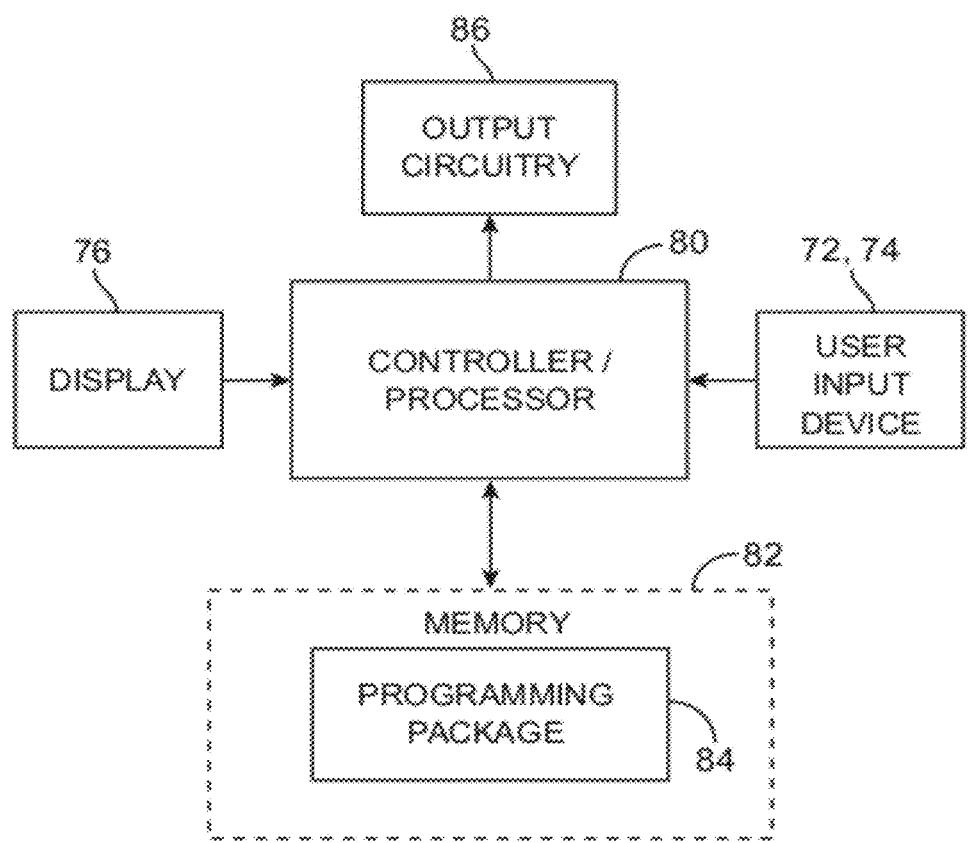
FIG. 6 is a block diagram of the internal components of a clinician's programmer (CP) used in the DBS system of FIG. 1.

Referring to FIG. 6, to allow the user to perform these functions, the CP 18 includes a standard user input device 72 (e.g., a keyboard, mouse, joystick, etc.) to allow a clinician to input information and control the process and a display monitor 76 housed in a case. In the illustrated embodiment, the monitor 76 is a conventional screen. Alternatively, instead of being conventional, the monitor 76 may be a digitizer screen, such as touchscreen (not shown), and may be used in conjunction with an active or passive digitizer stylus/finger touch. The CP 18 generally includes a controller/processor 80 (e.g., a central processor unit (CPU)) and memory 82 that stores a stimulation programming package 84, which can be executed by the controller/processor 80 to allow the user to program the IPG 14, and RC 16. The CP 18 further includes output circuitry 86 for downloading stimulation parameters to the IPG 14 and RC 16 and for uploading stimulation parameters already stored in the memory 66 of the RC 16, via the telemetry circuitry 68 of the RC 16. Notably, while the controller/processor 80 is shown in FIG. 6 as a single device, the processing functions and controlling functions can be performed by a separate controller and processor. Thus, it can be appreciated that the controlling functions described below as being performed by the CP 18 can be performed by a controller, and the processing functions described below as being performed by the CP 18 can be performed by a processor.

Execution of the programming package 84 by the controller/processor 80 provides a multitude of display screens (not shown) that can be navigated through via use of the user input device 72. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a therapeutic map (e.g., body regions targeted for therapy, body regions for minimization of side-effects, along with metrics (e.g., Unified Parkinson's Disease Rating Scale (UPDRS)) of success for said targets) of the patient, define the configuration and orientation of the leads, initiate and control the electrical stimulation energy output by the leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

Most pertinent to the present inventions, execution of the programming package 84 provides a more intuitive user interface that allows a user to readily determine the extent that to which specified electrodes influence one or more clinical effects (e.g., a therapeutic effect and/or side-effect), modify anatomical regions of interest (e.g., a therapy tissue region and/or a side-effect tissue region) to be specific to the patient, and/or matching a electric field, and thus the electrode combination that best generates the electric field, to a therapy tissue region.

The user interface includes a series of programming screens with various control elements that can be actuated to perform functions corresponding to the control elements. In the illustrated embodiment, control elements are implemented as a graphical icon that can be clicked with a mouse in the case of a conventional display device. Alternatively, the display device may have a digitizer screen (e.g., a touch-screen) that can be touched or otherwise activated with an active or passive digitizer stylus. More alternatively, the control elements described herein may be implemented as a joy stick, touchpad, button pad, group of keyboard arrow keys, mouse, roller ball tracking device, horizontal or vertical rocker-type arm switches, etc., that can be pressed or otherwise moved to actuate the control elements. Alternatively, other forms of entering information can be used, such as textual input (e.g., text boxes) or microphones.

Figure 7:
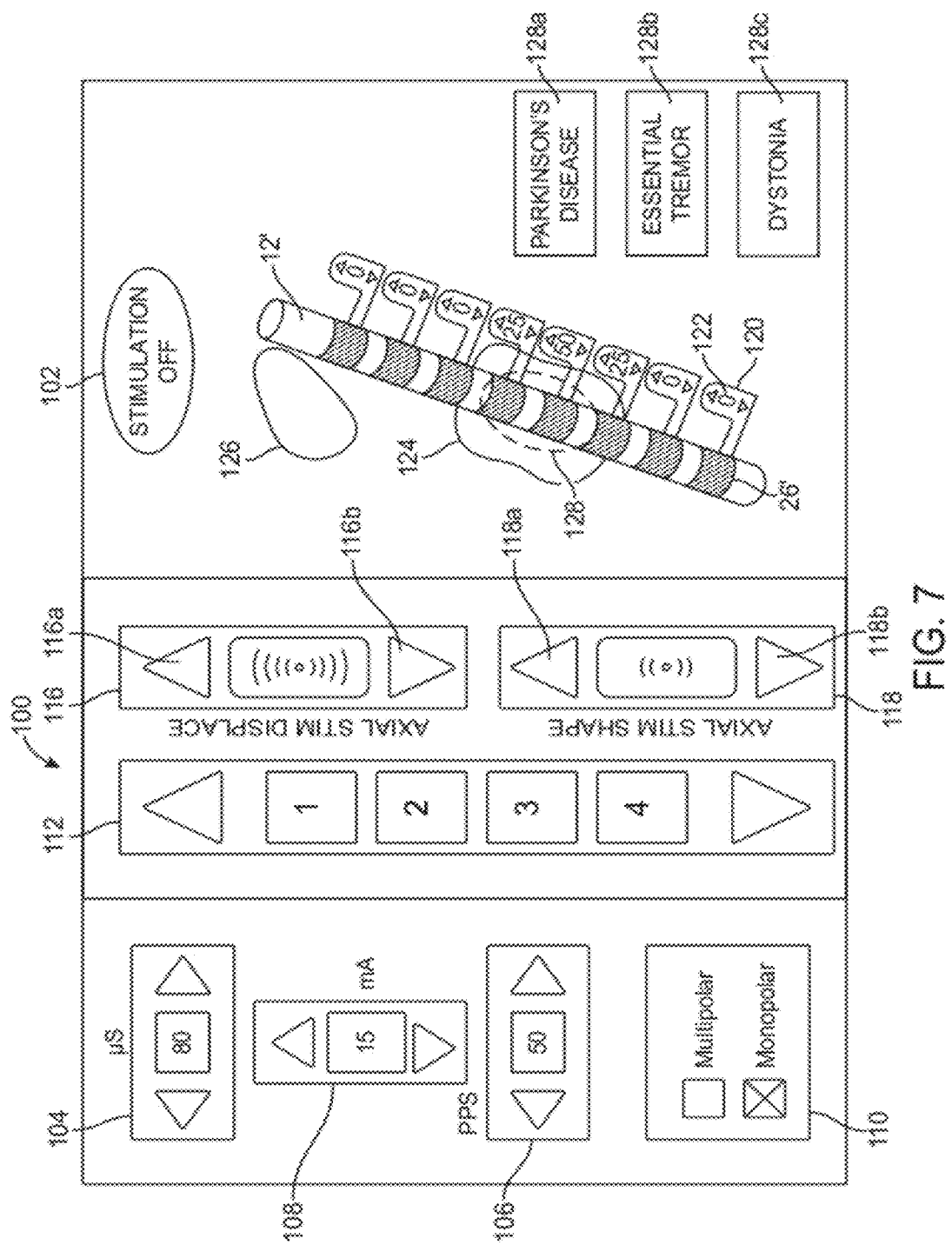
FIG. 7 is a plan view of a programming screen generated by the CP of FIG. 6 for programming the IPG of FIG. 3.

In particular, a programming screen 100 can be generated by the CP 18, as shown in FIG. 7. The programming screen 100 allows a user to perform stimulation parameter testing. To this end, the programming screen 100 comprises a stimulation on/off control 102 that can be alternately clicked to turn the stimulation on or off. The programming screen 100 further includes various stimulation parameter controls that can be operated by the user to manually adjust stimulation parameters. In particular, the programming screen 100 includes a pulse width adjustment control 104 (expressed in microseconds (µs)), a pulse rate adjustment control 106 (expressed in pulses per second (pps), and a pulse amplitude adjustment control 108 (expressed in milliamperes (mA)). Each control includes a first arrow that can be clicked to decrease the value of the respective stimulation parameter and a second arrow that can be clicked to increase the value of the respective stimulation parameter. The programming screen 100 also includes multipolar/monopolar stimulation selection control 110, which includes check boxes that can be alternately clicked by the user to provide multipolar or monopolar stimulation. In an optional embodiment, the case 40 of the IPG 14 may be treated as one of the lead electrodes 26, such that both the case electrode 40 and at least one of the lead electrodes 26 can be used to convey anodic electrical current at the same time. Additionally, the case electrode may be configured with all the programmability of a lead electrode, with full anodic and cathodic fractionalization.

The programming screen 100 also includes an electrode combination control 112 having arrows that can be clicked by the user to select one of four different electrode combinations 1-4. Each of the electrode combinations 1-4 can be created using a variety of control elements. The programming screen 100 also includes a set of axial electrical stimulation field displacement control elements 116 and a set of axial electrical stimulation field shaping control elements 118.

When any of the axial electrical stimulation field displacement control elements 116 is actuated, control signals are generated in response to which the controller/processor 80 is configured for generating stimulation parameter sets designed to axially displace the locus of the electrical stimulation field relative to the axis of the lead 12. Preferably, the control signals that are generated in response to the actuation of the axial electrical stimulation field displacement control elements 116 or the alternative control elements are directional, meaning that the locus of the electrical stimulation field will be displaced in a defined direction in response to a continual actuation of a single control element irrespective of the current position of the locus electrical stimulation field locus. When any of the axial electrical stimulation field shaping control elements 118 is actuated, control signals are generated in response to which the controller/processor 80 is configured for generating stimulation parameter sets designed to axially expand or contract the electrical stimulation field relative to its locus.

The control elements 116, 118 may be continually actuated (i.e., by continuously actuating one of the control elements 116, 118, e.g., by clicking on one of the control elements 116, 118 and holding the click (i.e., continuous actuation of the control following the initial "click"), or repeatedly actuating one of the control elements 116, 118, e.g., by repeatedly clicking and releasing one of the control elements 116, 118) to generate a series of control signals in response to which the controller/processor 80 is configured for generating the plurality of stimulation parameter sets. The output telemetry circuitry 86 is configured for transmitting these stimulation parameters sets to the IPG 14.

Each of the sets of control elements 116, 118 takes the form of a double arrow (i.e., two oppositely pointing control element arrows) that can be actuated to modify the electrical stimulation field depending on the mode of operation. For example, an upper arrow control element 116a can be clicked to axially displace the locus of the electrical stimulation field (i.e., along the axis of the lead 12) in the proximal direction; a lower arrow control element 116b can be clicked to axially displace the locus of the electrical stimulation field (i.e., along the axis of the lead 12) in the distal direction; a lower arrow control element 118a can be clicked to axially contract the electrical stimulation field about its locus, and an upper arrow control element 118b can be clicked to axially expand the electrical stimulation field about its locus.

The locus of the electrical stimulation field may be displaced, e.g., by gradually "steering" or shifting electrical current between electrodes in a single timing channel. For example, the locus of the electrical stimulation field can be gradually displaced axially in the distal direction along the lead 12 by gradually including electrodes in a stimulating electrode group and gradually excluding other electrodes from the stimulating electrode group in the single timing channel.

Although the programming screen 100 illustrates only one neurostimulation lead 12 with electrodes arranged in only one dimension, thereby allowing the electrical current to only be steered in one dimension, it should be appreciated that the programming screen 100 may additionally illustrate the other neurostimulation lead 12, thereby arranging the electrodes in two dimensions and allowing the electrical current to be steered in two dimensions. In this case, using appropriate control elements (e.g., left and right arrows), the locus of the electrical stimulation field can be displaced in the transverse direction (perpendicular to the axial direction, and in this case, left or right) and/or the electrical stimulation field can be expanded or contracted in the transverse direction. Of course, the electrodes can be arranged in three-dimensions (e.g., by arranging three neurostimulation leads in three-dimensions or by using electrodes on a single neurostimulation lead that are arranged in three-dimensions, e.g., the segmented neurostimulation leads described in U.S. Provisional Patent Application Ser. No. 61/374,879), in which case, the electrical current can be steering in three-dimensions.

Further details discussing different techniques for modifying an electrical stimulation field is disclosed in U.S. Provisional Patent Application 61/374,879, entitled "User Interface for Segmented Neurostimulation Leads," which is expressly incorporated herein by reference.

The programming screen 100 displays three-dimensional graphical renderings of the lead 12' and electrodes 26'. In an optional embodiment, iconic control elements 120 are graphically linked to the three-dimensional electrode renderings 26'. Continual actuation of the control elements 120 generates control signals that prompt the controller/processor 80 to generate stimulation parameters designed to modify the electrical stimulation field, which stimulation parameters are then transmitted from the output circuitry 86 of the CP 18 to the IPG 14. In the illustrated embodiment, each of the control elements 120 has an up arrow and a down arrow that can be respectively actuated (e.g., by clicking) to respectively increase or decrease the electrical current flowing through the electrode 26 corresponding to the graphical electrode rendering 26' to which the actuated control element 120 is graphically linked.

Actuation of any of the control elements 120 essentially steers electrical current from other active electrodes to the electrode associated with the actuated control element 120 or from the electrode associated with the actuated control element 120 to other active electrodes. In this manner, the locus of the electrical stimulation field can be displaced, the shape of the electrical stimulation field can be modified, and if two separate electrical stimulation fields current exist, electrical current can be shifted from one of the electrical stimulation fields (effectively decreasing its size) to another of the electrical stimulation fields (effectively increasing its size).

The control element 120 also includes an indicator 122 that provides an indication of the amount of electrical current flowing through each of the electrodes 26 in terms of a fractionalized current value. The indicators 122 may perform this function when the respective control elements 120 are actuated or when the axial electrical stimulation field displacement control elements 116 and axial electrical stimulation field shaping control elements 118 are actuated.

The programming screen 100 displays the three-dimensional graphical renderings of the lead 12' and electrodes 26' in registration with anatomical regions of interest, and in particular, a therapy tissue region 124, the stimulation of which is known or believed to provide the needed therapy to the patient, and a side-effect tissue region 126, the stimulation of which is known or believed to provide an undesirable side-effect for the patient. As will be described in further detail below, the anatomical regions of interest may be user-defined and have a spatial position linked to a reference, e.g., an atlas or reference points, such as the posterior commissural point, anterior commissural point, mid-commissural point, and/or mid-sagittal plane. By having the shape linked to an anatomical reference, it may be transformed with the anatomical reference (e.g., if an atlas is registered to patient radiographic data then the shape could also undergo the registration and would be available in patient-specific form for use with that patient). In the illustrated embodiment, the anatomical regions of interest are shown as being two-dimensional, although in other embodiments, the anatomical regions of interest may be three-dimensional in nature.

Various anatomical regions of interest, which may be associated with different ailments to be treated, may be stored memory 82 and subsequently recalled via operation of therapy selection elements 128a, 128b, 128c. For example, if the therapy selection element 128a, the anatomical regions of interest associated with Parkinson's Disease can be recalled from the memory 82 and displayed on the programming screen 100. If the therapy selection element 128b, the anatomical regions of interest associated with Essential Tremor can be recalled from the memory 82 and displayed on the programming screen 100. If the therapy selection element 128c, the anatomical regions of interest associated with Dystonia can be recalled from the memory 82 and displayed on the programming screen 100.

Based on the current stimulation parameter set, the CP 18 may estimate of a resulting stimulation field model (SFM) 130, which can be displayed on the programming screen 100 with the graphical lead 12' and anatomical regions of interest 124, 126. Further details discussing technique for computing the estimate of a SFM 130 are disclosed in A. M. M. Frankemolle, et al., *Reversing Cognitive-Motor Impairments in Parkinson's Disease Patients Using a Computational Modelling Approach to Deep Brain Stimulation Programming*, Brain 2010; pp. 1-16), which is expressly incorporated herein by reference.

Alternatively, instead of computing and displaying a SFM, the CP 18 may compute an electric field (not shown) from the current stimulation parameter set, which may be displayed relative to the graphical lead 12' and anatomical regions of interest 124,126. In the illustrated embodiment, although the graphical lead 12', anatomical regions of interest 124,126, and the SFM 130 are displayed in an oblique view, they can be alternatively displayed in any one or more of traditional planes of section (e.g., axial, coronal, and sagittal).

Figure 8:
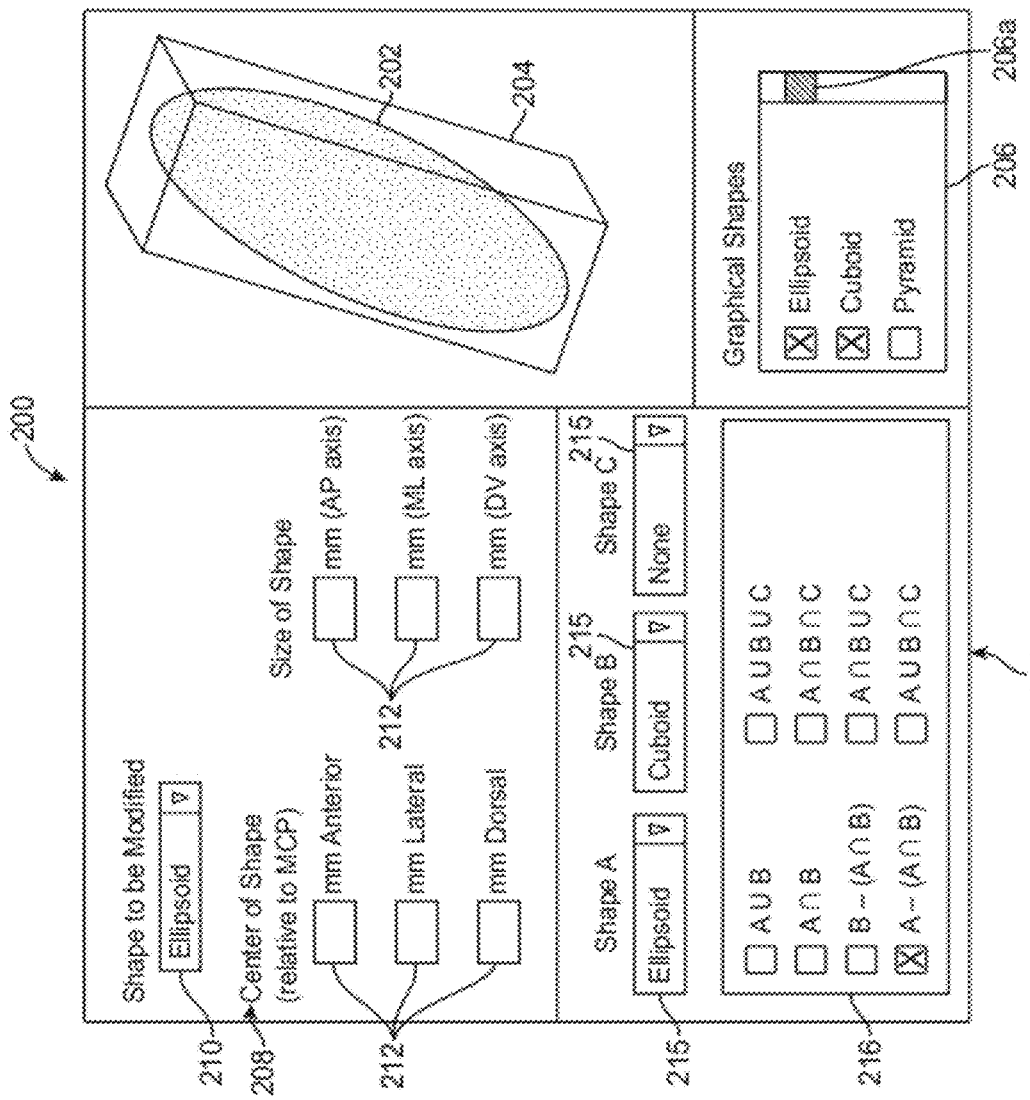
FIG. 8 is a plan view of one embodiment of an anatomical region of interest definition screen generated by the CP of FIG. 6 for defining a graphical shape representative of an anatomical region of interest for subsequent visualization in the programming screen illustrated in FIG. 7.

Referring now to FIG. 8, an anatomical region of interest definition screen 200 will be described. The screen 200 includes a listing of predefined graphical shapes 206. In the illustrated embodiment, the listed pre-defined graphical shapes 206 can be stored in the memory 82 during manufacture, but alternatively may be defined by the user and then stored in memory. Each graphical shape from the graphical shape listing 206 represents an anatomical region of interest, such as a therapy region, a side-effect region, or other relevant reference information, that can be used as a visualization aid by the user when programming the IPG 14. As will be described in further detail below, based on the shape and location of an anatomical region of interest, a graphical shape is selected from the graphical shape listing 206 and located in the screen 200 relative to an anatomical reference, such as an atlas or one or more anatomical points of reference. Preferably, the graphical shape and its location are chosen to best match the shape and location of the anatomical reference.

The graphical shape listing 206 may contain many different types of predefined graphical shapes. Types of graphical shapes that may be in the graphical shape listing 206 include, but are not limited to, regular two-dimensional shapes (e.g., circle, square, and triangle), irregular two-dimensional shapes, regular three-dimensional shapes (e.g., ellipsoid, cuboid, and pyramid), and irregular three-dimensional shapes. Further the purposes of this specification, a "regular shape" is a symmetrical shape that has sides of equal lengths and angles of equal sizes, while an "irregular shape" has sides with different lengths and angles of different sizes. In addition, shapes that have rounded sides and are symmetrical (e.g., a circle, an oval, a sphere, and an ellipsoid) are considered to be "regular shapes." The user may select one or more of these graphical shapes from the listing 206 to be displayed on screen 200 relative to a reference, such as an atlas or anatomical reference points.

The screen 200 also includes a slide bar 206a, which may be slid up and down. When the user slides slide bar 206a up and down, the user is able to scroll up and down through the entire listing 206 of predefined graphical shapes. Each graphical shape in the listing 206 has its own check box that can be alternately clicked by the user to display or not display that particular graphical shape on the screen 200. In this example, the check box of an ellipsoid graphical shape is shown to be checked in the listing 206. In response to the check box for an ellipsoid in the listing 206 being checked, an ellipsoid graphical shape 202 is displayed on the screen 200. If the check box for the cuboidal graphical shape is checked, a cuboidal graphical shape 204 is displayed on the screen 200. It should be noted that in alternative embodiments, the graphical shape listing 206 may be implemented in the screen 200 by a drop-down menu, or some other means, rather than a slide bar list with check boxes as is shown in FIG. 8.

Rather than provide a means for the user to select one or more predefined shapes, the screen 200 may alternatively provide other means for the user to define new graphical shapes. One way for the user to define a new graphical shape is for the user to simply draw a two-dimensional graphical shape on the screen 200 by using a touch pad screen, joystick, arrow buttons, textual input, and/or some other means. This method might be particularly useful when the user wants to define a volume of interest using a radiographic image or an atlas as a reference. For example, the user may define (e.g., by drawing) a region on one or more slices of a radiographic volume, or perhaps on one or more slices of atlas, and the areas defined on the slices might be converted to 3D volumes by extrapolation or interpolation (or left as 2D areas). For example, as shown in FIG. 13, a two-dimensional graphical shape 236 can be drawn on an axial view of an MRI and/or a two-dimensional graphical shape 238 can be drawn on a coronal view of an MRI. Additional two-dimensional graphical shapes 236, 238 can be draw on different axial or coronal views of the MRI. A 3D volume can then be extrapolated or interpolated from the two-dimensional shapes 236, 238.

Still another way for the user to define a new graphical shape is for the user to import a graphical shape along with the spatially linked anatomical reference from another device. Types of devices that may be used to obtain a graphical shape include, but are not limited to, another CP that is used to capture a stimulation field model that can be used as a graphical shape representing an estimated therapy region, or capture a user-defined graphical shape that represents a region of interest, or as described below, the CP could perform analytics (e.g., statistical evaluations) on data from multiple patients and capture the resulting spatial data and/or shapes. Further, a computer running computer-aided design (CAD) software could be used to create a CAD generated graphical shape that is importable to the CP 18.

For example, a different CP enabled with the programming screen 100 illustrated in FIG. 7 can be used to capture a specific stimulation field model during a programming session for a patient, and then imported into the current CP 18 as a graphical shape for representation as an anatomical region of interest. Alternatively, rather than basing the graphical shape on a single programming session, the graphical shape can be obtained from a population analysis of stimulation field models. In any event, the graphical shape and spatially linked anatomical reference may be saved in the form of a file (e.g., to a thumb drive, hard disk, etc.), as a text code (e.g., a compressed code that defines the candidate graphical shape), as a graphical code, audio code, or other encoded format. The graphical shape generated by the other CP may be represented in a variety of manners.

For example, the graphical shape may be a position indicator relative to the anatomical reference, an orientation indicator (e.g., angular, such as azimuth and elevation) relative to the anatomical reference, a mesh with nodes and elements (surface or volume), geometrical primitives with appropriate definitions (e.g., sphere—diameter; ellipsoid—axes lengths; hexagon—side-lengths; pyramid—height, lower radius, upper radius; etc.), other manipulations of geometrical primitives, such as warping parameters (e.g., amount of warp, direction of warp, etc.) or Booleans of geometrical primitives, identification of elements, voxels, or nodes that are included with or excluded from the graphical shape, definition of grid properties (e.g., resolution, size, position, orientation, etc.), definition of grid properties (e.g., resolution, size, position, orientation, etc.) in addition to grid values, values (discrete or continuous variable) for grid points (or elements or voxels), or a threshold, which may be useful where values have been assigned (user may be given ability to change threshold).

The current CP 18 can accept the graphical shape and anatomical reference from the other CP in the form of a file (e.g., from a thumb drive, on-line download, etc.) as a text input code (e.g., a compressed code that defines a candidate graphical shape), as a graphical input code, audio input code, or other encoded format. Once entered, the candidate graphical shape is visualizable on the screen 200. Alternatively, the current CP 18 may use the graphical shape imported from the other CP to allow modification of a graphical shape currently stored in the current CP 18, and in particular, modifications of size, shape, position, color, and/or lighting of the graphical shape relative to the anatomical reference.

Another way for a user to define a new graphical shape is to capture the SFM being used by a patient, perhaps from the programming screen 100. This method might be useful when a particular patient has a particularly positive response, and the clinician would like to reproduce that stimulation in other patients. Note that the SFM might be initially captured in the patient's coordinate system, and then readily transformed back into atlas-space or a general MCP-space, thus making it easy to use with subsequent patients.

Still another way for the user to define a new graphical shape is for the user to apply at least one Boolean function to a plurality of selected predefined graphical shapes using graphical control elements, as will be described in further detail below.

In addition to allowing the user to select one of the graphical shapes from the listing 206, the screen 200 includes a graphical shape modification control box 208 used for sizing and/or translating selected graphical shapes relative to an anatomical reference, such as an atlas or anatomical reference points. Rotation might also be used to move the graphical shape.

For example, the user may specify a size and/or position of a selected graphical shape or shapes. In particular, a drop-down menu 210 may be used to select the specific graphical shape that the user desires to modify. Textual input boxes 212 can be used by the user to enter numerical values to specify the location of the center of the selected graphical shape and/or the size of the selected graphical shape. For an example case, a user may wish to modify the location and size of an ellipsoidal graphical shape. In order to do so, the user must first select the ellipsoid shape by using the drop down menu 210 for the shape to be modified. Then, the user can specify the anterior, lateral, and dorsal coordinates for the location of the center point of the selected ellipsoidal graphical shape by typing the specific numerical values in the appropriate textual input boxes 212. The user can then specify the size of the selected ellipsoidal shape relative to the anterior-posterior (AP), medial-lateral (ML), and dorsal-ventral (DV) axis by typing the specific numerical values in the appropriate textual input boxes 212. The anatomical reference will be registered in the coordinate system defined by the AP, ML, and DV axes, and thus, the modified graphical shape will be registered with the anatomical reference.

Figure 9:
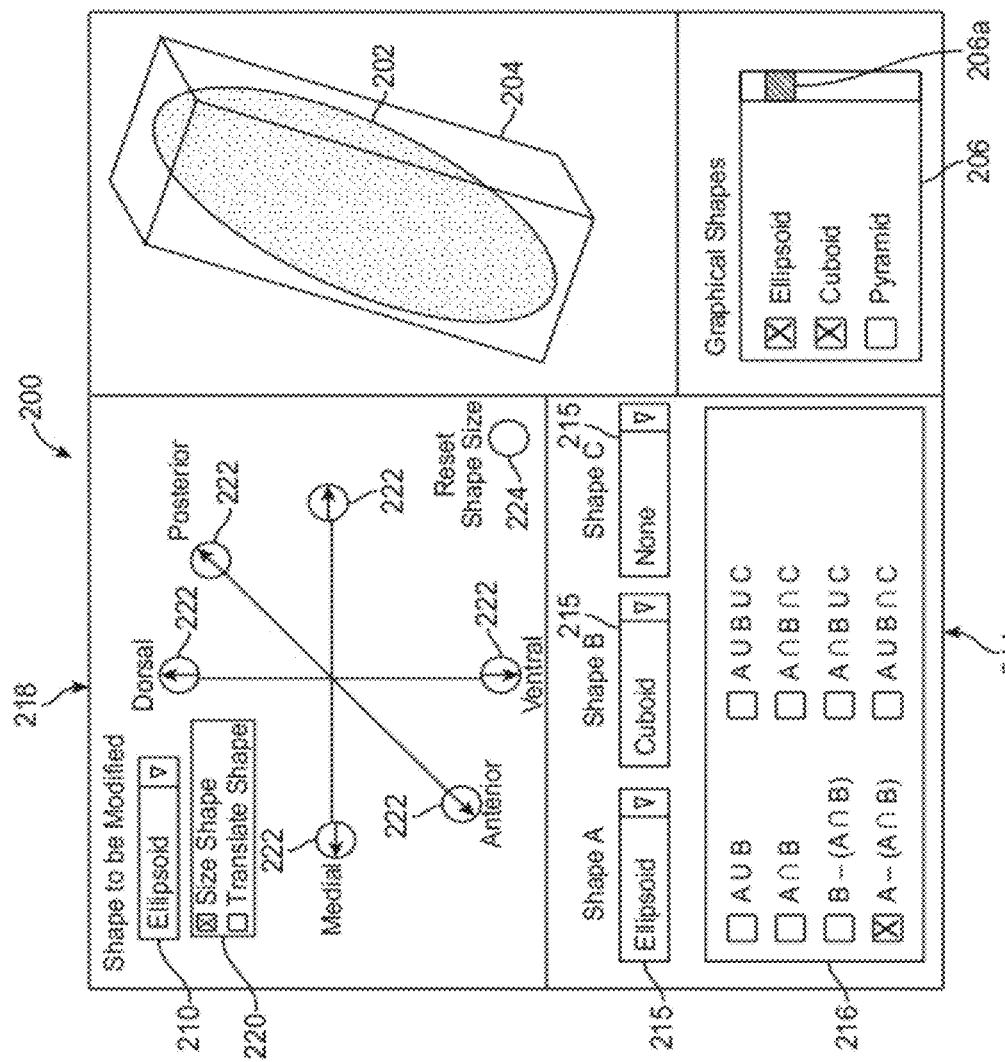
FIG. 9 is a plan view of another embodiment of an anatomical region of interest definition screen generated by the CP of FIG. 6 for defining a graphical shape representative of an anatomical region of interest for subsequent visualization in the programming screen illustrated in FIG. 7.

In an alternative embodiment shown in FIG. 9, the screen 200 may include a different graphical shape modification control box 218 that can be used for sizing and/or translating selected graphical shapes relative to an anatomical reference, such as an atlas or anatomical reference points. The shape modification control box 218 includes button controls 220 for specifying a size and/or position of a selected graphical shape or shapes. Similar to FIG. 8, the graphical shape modification box 218 of FIG. 9 includes a drop-down menu 210 that enables the user to select the specific graphical shape that the user wishes to modify. The graphical shape modification box 218 also includes a bank of check boxes 220 that can be alternately clicked by the user to choose to modify the size or modify the location of the selected graphical shape on the screen 200.

If the check box for sizing the shape is checked, the button controls 222 will be switched to a mode for modifying the size of the selected graphical shape. In contrast, if the check box for translating the shape is checked, the button controls 222 will be switched to a mode for modifying the location of the selected graphical shape. For example, the graphical shape modification control box 218 shows that the check box for modifying the size of the selected graphical shape is checked and, thus, the button controls 222 are switched to a mode for modifying the size of the selected ellipsoidal graphical shape. By continually actuating the buttons 222 (i.e. by continuously actuating one of the buttons 222 by clicking on the button 222 and holding the click) or repeatedly actuating the buttons 222 (i.e. by repeatedly clicking and releasing one of the buttons 222), the user is able to alter the size and/or the location of the selected graphical shape accordingly.

The graphical shape modification control box 218 also includes a Reset Shape Size button 224, which allows the user to reset the size of the selected graphical shape to its original size after the user has enlarged the selected graphical shape using one or more of the button controls 222. As such, by simply actuating this button 224 (i.e. clicking the button 224), the user is able to instantly shrink the selected graphical shape back to the size that it originally was before it was enlarged by the user.

Figure 10:
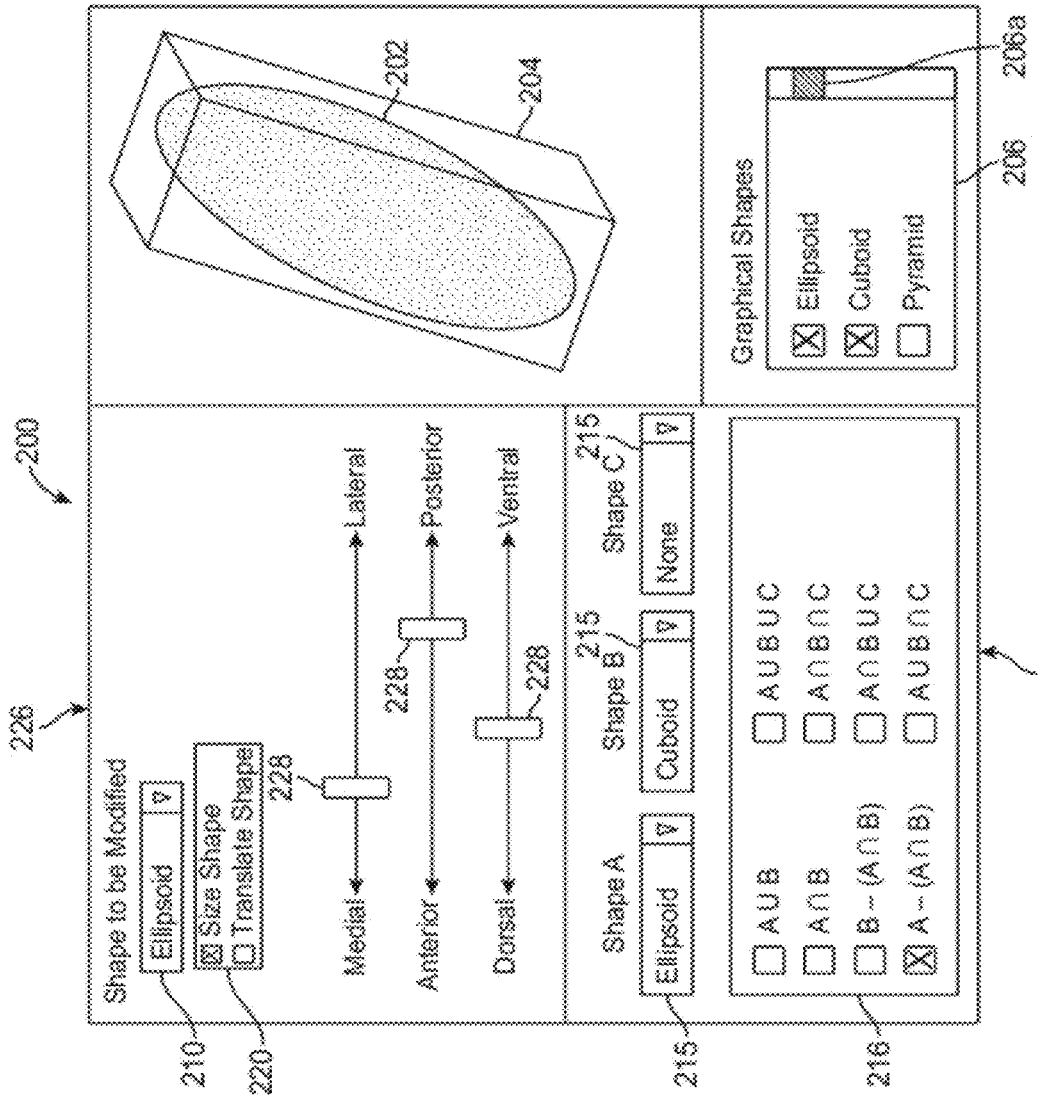
FIG. 10 is a plan view of still another embodiment of an anatomical region of interest definition screen generated by the CP of FIG. 6 for defining a graphical shape representative of an anatomical region of interest for subsequent visualization in the programming screen illustrated in FIG. 7.

In an alternative embodiment shown in FIG. 10, the screen 200 may include slide bar control box 226 that can be used to specify a size and/or position of a selected graphical shape or shapes. Similar to the embodiments of FIGS. 8 and 9, a drop-down menu 210 is provided that allows the user to select the specific graphical shape that the user would like to modify. Also, similar to FIG. 9, the graphical shape modification box 226 of FIG. 10 includes a bank of check boxes 220 that may be alternately clicked by the user to choose to modify the size or modify the location of the selected graphical shape on the screen 200. Once the user has selected the graphical shape and checked the appropriate check box, the user can slide the slide controls 228 to the left and/or the right to modify the size and/or the location of the selected graphical shape accordingly.

For example, if a user desires to modify the size of an ellipsoidal graphical shape, the user must first select the ellipsoid shape by using the drop down menu 210 for the shape to be modified. Then, the user must click on the size shape check box 220 in order choose to modify the size of the selected ellipsoidal graphical shape. After the user has clicked on the size shape check box 220, the slide controls 228 will be in a mode to modify the size of the ellipsoidal shape. The user can then specify the size of the ellipsoidal shape relative to the ML, AP, and DV axis by sliding each corresponding slide bar 228 accordingly.

Referring to any of the embodiments illustrated in FIGS. 8-10, the screen 200 includes Boolean function graphical shape control box 214, which is used for employing Boolean functions to define a new graphical shape or shapes. The Boolean function graphical shape control box 214 includes three drop-down menus 215 for Shape A, Shape B, and Shape C, respectively. Each of these drop-down menus is for selecting a specific graphical shape that a Boolean function is to be applied. In this example, an ellipsoid is selected for Shape A, a cuboid is selected for Shape B, and no shape is selected for Shape C. It should be noted that for other embodiments, various numbers of drop-down menus may be employed.

Figure 11:
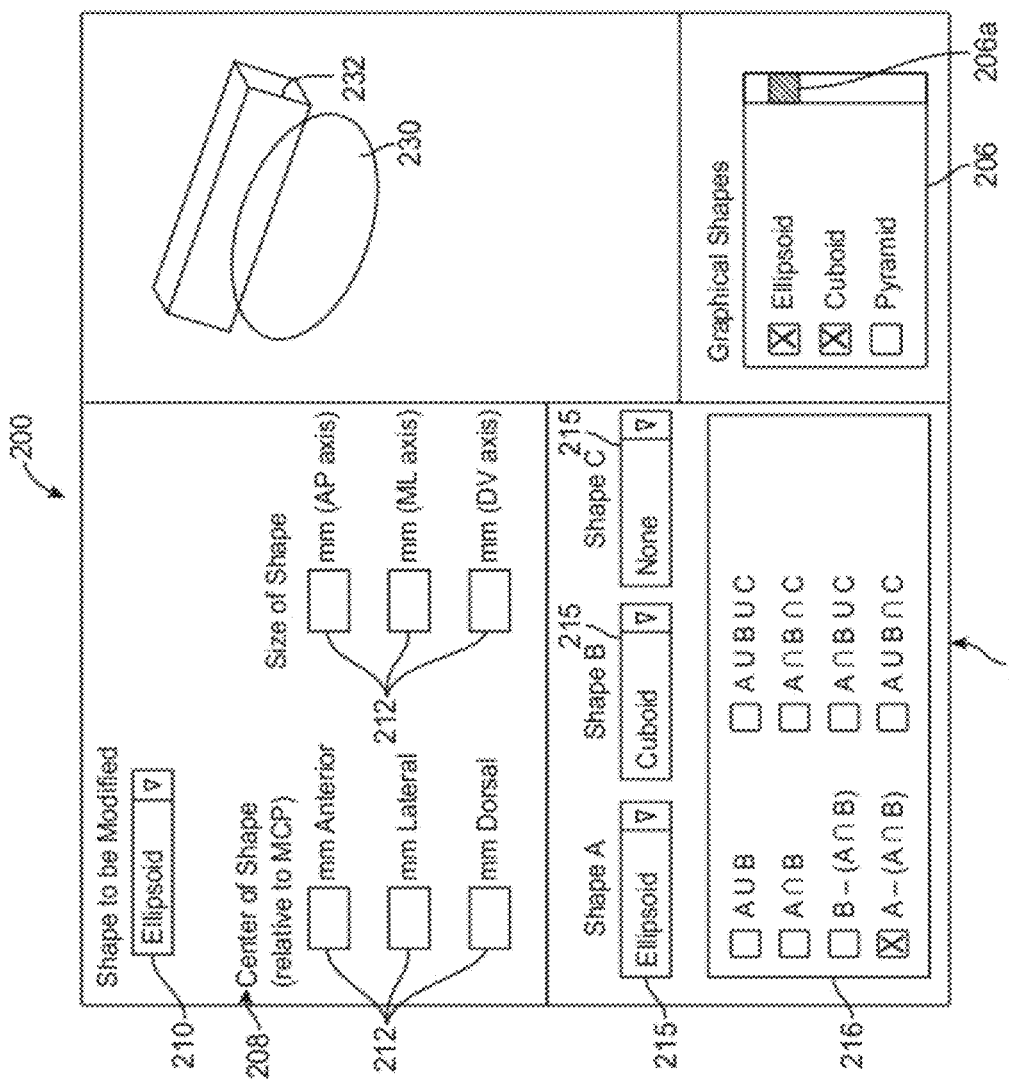
FIG. 11 is a plan view of yet another embodiment of an anatomical region of interest definition screen generated by the CP of FIG. 6 for defining a graphical shape representative of an anatomical region of interest for subsequent visualization in the programming screen illustrated in FIG. 7.

The Boolean function graphical shape control box 214 also includes check boxes 216 for selecting a specific Boolean function to be applied to the selected graphical shapes for Shape A, Shape B, and Shape C. In this example, a check box for Boolean function A−(A∩B) is checked and, thus, this Boolean function will be applied to ellipsoid Shape A and cuboid Shape B, as shown in FIG. 11. It should be noted that in other embodiments of the present disclosure, various different Boolean functions may be implemented in the Boolean function graphical shape control box 214 than are depicted in FIG. 11. Different types of Boolean functions that may be employed by the Boolean function graphical shape control box 214 include, but are not limited to, A∪C, A∩C, B∪C, B∩C, C−(A∩C), C−(B∪C), A∩C∪B, and A∪C∩B.

Figure 12:
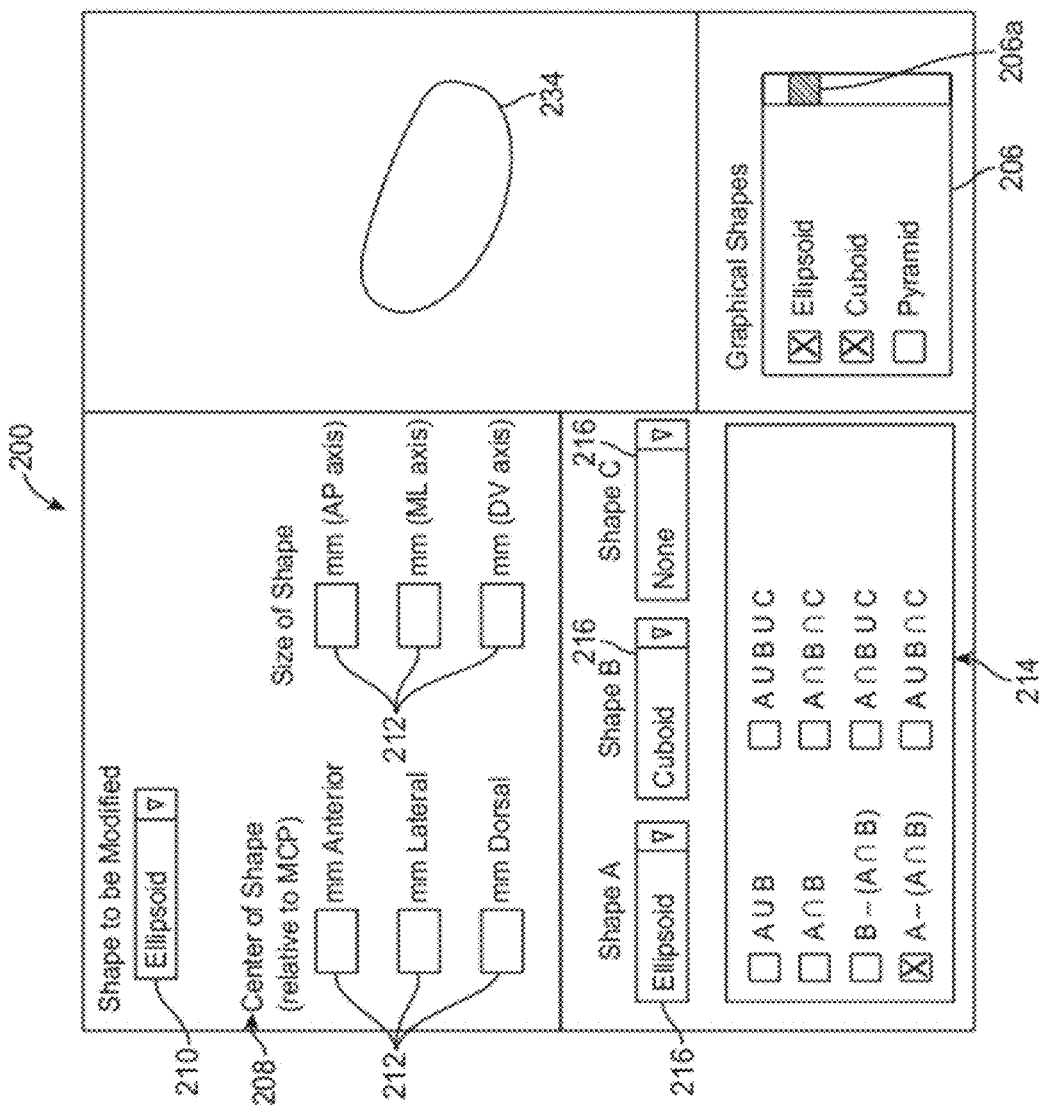
FIG. 12 is a plan view of the anatomical region of interest definition screen of FIG. 11, particularly showing a resulting graphical shape.

The example illustrated in FIGS. 11 and 12 shows how a user can apply a Boolean function to two selected graphical shapes from the drop-down menus 215 in order to generate a new graphical shape. In particular, the screen 200 displays a selected ellipsoidal graphical shape 230 and a selected cuboidal graphical shape 232. The Boolean function graphical shape control box 214 shows that the user selected the ellipsoid for Shape A and the cuboid for Shape B. Also, the Boolean function graphical shape control box 214 shows that the user selected Boolean function A−(A∩B) to be applied to Shape A (i.e. the ellipsoid) and to Shape B (i.e. the cuboid). The programming screen 200 depicted in FIG. 12 shows the resulting graphical shape 234 (i.e. an ellipse-cuboid) that is created after that particular Boolean function is applied to the ellipsoid and the cuboid.

Although the foregoing techniques have been described as being implemented in the CP 18, it should be noted that this technique may be alternatively or additionally implemented in the RC 16, and the processing functions of the technique can even be performed in the IPG 14. Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A system for programming a neurostimulation device coupled to one or more electrodes, comprising:
   a user interface configured for allowing a user to select a set of stimulation parameters and to define one of a plurality of different graphical shapes, each representative of an anatomical region of interest;
   memory configured for storing the defined graphical shape with a spatial position linked to an anatomical reference;
   output circuitry configured for communicating with the neurostimulation device; and
   a controller configured for recalling the linked graphical shape and anatomical reference from the memory, generating display signals capable of prompting the user interface to concurrently display a representation of the one or more electrodes relative to the recalled graphical shape, and programming the neurostimulation device with the selected stimulation parameter set via the output circuitry.

2. The system of claim 1, wherein the anatomical region of interest is a therapy region.

3. The system of claim 1, wherein the anatomical region of interest is a side-effect region.

4. The system of claim 1, wherein the display signals are capable of prompting the user interface to further display the representation of the one or more electrodes relative to the anatomical reference.

5. The system of claim 4, wherein the anatomical reference is an atlas.

6. The system of claim 5, wherein the anatomical reference comprises one or more anatomical reference points.

7. The system of claim 6, wherein the one or more anatomical reference points comprises at least one of a posterior commissural point, anterior commissural point, and a mid-commissural point.

8. The system of claim 1, wherein the defined graphical shape is a three-dimensional graphical shape.

9. The system of claim 1, wherein the defined graphical shape is a regular three-dimensional geometric shape.

10. The system of claim 9, wherein the regular three-dimensional geometric shape is one of an ellipsoid, a cuboid, and a pyramid.

11. The system of claim 1, wherein the memory stores a plurality of predefined graphical shapes respectively representing anatomical regions of interest, and the user interface is further configured for allowing the user to select the graphical shape from the plurality of predefined graphical shapes.

12. The system of claim 1, wherein the user interface is configured for allowing the user to define the graphical shape by allowing the user to draw a two-dimensional graphical shape.

13. The system of claim 12, further comprising a processor configured for extrapolating a three-dimensional graphical shape from the drawn two-dimensional shape.

14. The system of claim 1, wherein the user interface is configured for allowing the user to define the graphical shape by allowing the user to import a graphical shape from another device.

15. The system of claim 1, wherein the further comprising a processor configured for generating a stimulation field model based on the selected stimulation parameter set, and the user interface is configured for allowing the user to define the graphical shape by allowing the user to select the stimulation field model as the graphical shape.

16. The system of claim 1, wherein the user interface is configured for allowing the user to define the graphical shape by allowing the user to apply a Boolean function to a plurality of predefined graphical shapes to create the defined graphical shape.

17. The system of claim 1, wherein the user interface is further configured for allowing the user to define a location of the defined graphical shape relative to the representation of the one or more electrodes.

18. The system of claim 1, wherein the user interface is further configured for allowing the user to change a size of the defined graphical shape.

19. The system of claim 1, further comprising a processor configured for generating a stimulation field model based on the selected stimulation parameter set, wherein the controller is configured for generating display signals capable of prompting the user interface to concurrently display the generated stimulation field model relative to the recalled graphical shape and anatomical reference.

20. The system of claim 1, further comprising an external control device comprising the user interface, memory, output circuitry, and controller.

21. The system of claim 1, further comprising the neurostimulator.

22. The system of claim 1, wherein the output circuitry comprises telemetry circuitry.

* * * * *